US008236848B2

(12) United States Patent
Zeligs

(10) Patent No.: US 8,236,848 B2
(45) Date of Patent: *Aug. 7, 2012

(54) DIINDOLYLMETHANE FOR THE TREATMENT OF HPV INFECTION

(75) Inventor: Michael A. Zeligs, Boulder, CO (US)

(73) Assignee: BioResponse, L.L.C., Boulder, CO (US)

( * ) Notice: Subject to any disclaimer, the term of this patent is extended or adjusted under 35 U.S.C. 154(b) by 730 days.

This patent is subject to a terminal disclaimer.

(21) Appl. No.: 12/070,115

(22) Filed: Feb. 14, 2008

(65) Prior Publication Data

US 2008/0145418 A1   Jun. 19, 2008

Related U.S. Application Data

(62) Division of application No. 10/117,288, filed on Apr. 5, 2002, now Pat. No. 7,348,352.

(60) Provisional application No. 60/337,563, filed on Oct. 23, 2001.

(51) Int. Cl.
*A61K 31/405* (2006.01)
*A61K 31/40* (2006.01)
*A61K 9/48* (2006.01)
*A61K 9/20* (2006.01)
*A61K 9/14* (2006.01)
*A61K 33/00* (2006.01)

(52) U.S. Cl. ........ 514/415; 514/412; 514/414; 424/451; 424/464; 424/484; 424/744

(58) Field of Classification Search ............... 514/41, 514/412, 414, 415; 424/744, 451, 464, 484
See application file for complete search history.

(56) References Cited

U.S. PATENT DOCUMENTS

| | | | | |
|---|---|---|---|---|
| 5,820,870 | A * | 10/1998 | Joyce et al. | 424/204.1 |
| 5,830,887 | A | 11/1998 | Kelly | |
| 5,895,787 | A | 4/1999 | Arffmann et al. | |
| 5,948,808 | A | 9/1999 | Safe | |
| 6,086,915 | A | 7/2000 | Zeligs | |
| 6,399,645 | B1 | 6/2002 | Bell et al. | |
| 6,534,085 | B1 | 3/2003 | Zeligs | |
| 6,613,792 | B1 | 9/2003 | Ellenberger et al. | |
| 6,689,387 | B1 | 2/2004 | Zeligs | |
| 7,348,352 | B2 * | 3/2008 | Zeligs | 514/416 |
| 7,384,971 | B2 * | 6/2008 | Zeligs | 514/419 |
| 2002/0147155 | A1 | 10/2002 | Foster et al. | |
| 2004/0072891 | A1 | 4/2004 | Zeligs | |
| 2004/0156910 | A1 | 8/2004 | Zeligs | |

OTHER PUBLICATIONS

Bradlow et al. 'Multifunctional aspects of the action of indole-3-carbinol as an antitumor agent,' Annals of New York Academy of Sciences, 1999, vol. 889, pp. 204-213.*
Arbeit, JM et al., "Chronic estrogen-induced cervical and vaginal squamous carcinogenesis in human papillomavirus type 16 transgenic mice", Apr. 1996, Proc Natl Acad Sci, USA 93:2930-2935.
Auborn et al., 2000, "Treatment of Human Papillomavirus Gynecologic Infections", Clin Lab Med 20:407-22.
Baugh SM et al., "Treatment of cervical dysplasia with indole-3-carbinol" in the Ray A. Barlow Scientific Symposium, Jan. 23, 1998, Shreveport : The Center for Excellence in Cancer Research, Treatment and Education, Louisiana State University Medical Center, Shreveport (LA), p. 3.
Bell, MC et al., "Placebo-controlled Trial of Indole-3-Carbinol in the Treatment of Cervical Dysplasia", Mar. 1999, Gynecol. Oncol. 72:446.
Bell, MC et al., "Placebo-Controlled Trial of Indole-3-Carbinol in the Treatment of CIN", 2000, Gynecologic Oncology, 78:123-129.
BioResponse-DIM Indolplex Product Information Brochure, Dec. 15, 1998.
Bjeldanes et al., 1991, "Aromatic hydrocarbon responsiveness-receptor agonists generated from indole-3-carbinol in vitro and in vivo: comparisons with 2.3,7,8,-tetrachlorodibenzo-p-dioxin," Proc. Natl. Acad. Sci. USA 88:9543-9547.
Bradfield et al., "High-performance liquid chromatographic analysis of anticarcinogenic indoles in *Brassica oleracea*", 1987, J Agric Food Chem 35:46-49.
Bradlow et al., "2-hydroxyestrone: the 'good' estrogen", 1996, J Endocrin 150:S259-S265.
Cancer Medicine 3rd edition, 1993, JF Holland ed., Lea & Febiger, Malvern, PA p. 1633.
Chang et al., 1999, "Cytostatic and antiestrogenic effects of 2-(Indol-3-ylmethyl)-3,3'-diindolylmethane, a major in vivo product of dietary indole-3-carbinol," Biochem. Pharmacol. 58:825-834.
Chen et al., "Aryl hydrocarbon receptor-mediated antiestrogenic and antitumorigenic activity of diindoylmethane", 1998, Carcinogenesis 19:1631-1639.
Dashwood, R.H., 1998, "Indole-3-carbinol: anticarcinogen or tumor promoter in brassica vegetables?" Chem Biol. Interact., 110(1-2):1 -5.
de Vet et al., 1994, "The role of cigarette smoking in the etiology of cervical dysplasia," Epidemiology 5:631-633.
Dec. 1998 Bioresponse Letter, Dec. 29, 1998.
Exon, et al., 2000, "Dietary indole-3-carbinol alters immune functions in rats," J. Toxicol. Environ. Health A., 59(4):271-9.
Gillner et al.. 1985. "Interactions of indoles with specific binding sites for 2,3,7,8-tetrachlorodibenzo-p-dioxin in rat liver," Mol Pharmacol 28:357-363.
Gooptu et al., 2000, "Treatment of viral warts with cimetidine: and open-label study," Clin. Exp. Dermatol. 25(3):183-5.
Hardman et al. "Goodman & Gilman's The Pharmacological Basis of Therapeutics" (9th ed, 1996) p. 51 and 57-58.
Ho et al., "Urinary 2/16alpha-hydroestrone ratio: correlation with serum insulin-like growth factor binding protein-3 and a potential biomarker of breast cancer risk", 1998, Ann Acad Med Singapore 27:294-9.
Jin et al., "Indole-3-carbinol prevents cervical cancer in human papillomavirus type 16 (HPV16) transgenic mice", 1999, Cancer Res 59"3991-7.

(Continued)

Primary Examiner — Shengjun Wang
(74) Attorney, Agent, or Firm — Jones Day

(57) ABSTRACT

New methods and compositions are disclosed that comprise the phytochemical Diindolylmethane, alone or in combination with immune potentiating steroids. These methods and compositions are utilized to treat subjects suffering from common cutaneous warts (verrucae) and Human Papilloma Virus (HPV) related conditions of the oropharynx, larynx, genitalia, and uterine cervix.

31 Claims, No Drawings

OTHER PUBLICATIONS

Komura et al., "Catecholestrogen as a natural antioxidant", 1996, Ann NY Acad Sci 786:419-29.

Larson-Su et al., 2001, "Transplacental exposure to indole-3-carbinol induces sex-specific expression of CYPIAI and CYPIBI in the liver of Fischer 344 neonatal rats," Toxicological Sci. 64:162-168.

Liu et al., 1994, "Indolo[3,2-b]carbozole: a dietary-derived factor that exhibits both antiestrogenic and estrogenic activity," J. Natl. Cancer Inst. 86:1758-1765.

Loub et al., 1975, "Aryl hydrocarbon hydroxylase induction in rat tissues by naturally occurring indoles of cruciferous plants," J. Natl. Cancer Inst. 54:985-988.

Michnovicz et al., "Changes in levels of urinary estrogen metabolites after oral indole-3-carbinol treatment in humans", 1997, J Natl Cancer Inst 89:718-23.

Michnovicz et al., 1986, "Increased 2-hydroxylation of estradiol as a possible mechanism for the anti-estorgenic effect of cigarette smoking," N Engl J Med 315:1305-1309.

Michnovicz et al., 1988, "Increased urinary catechol estrogen excretion in female smokers," Steroids 52:69-83.

Michnovicz et al., 1991, "Cimetidine inhibits catechol estrogen metabolism in women," Metabolism, 40(2):170-74.

Molecular Biology of the Cell $2^{nd}$ ed., 1989, Alberts, B et al., Garland Publishing, Inc., New York, pp. 1193-1194, 1204-1206.

Ponten J and Guo Z, "Precancer of the Human Cervix", 1998, Cancer Surveys 32:201-229.

Riby et al., 2000, "Ligand-independent activation of estrogen receptor function by 3,3'-diindolylmethane in human breast cancer cells," Biochem. Pharmacol. 60:167-177.

Ritter et al., 2001, "Oxidations of 17beta-estradiol and estrone and their interconversions catalyzed by liver, mammary gland and mammary tumor after acute and chronic treatment of rats with indole-3-carbinol or beta-naphthoflavine," Can. J. Physiol. Pharmacol. 79(6):519-32.

Rosen et al., "Preliminary results of the use of indole-3-carbinol for recurrent respiratory papillomatosis", 1998, Otolaryngol Head Neck Surg 118:810-5.

Schneider et al., "Abnormal oxidative metabolism of estradiol in women with breast cancer", 1982, Proc Natl Acad Sci USA 79:3047-52.

Schwartz et al. Journal of Cellular Biochemistry, (1995) 581 Suppl. 22, (210-217).

Sepkovic et al., 2002, "Quantitative Determination of 3,3'-Diindolymethane in the urine of individuals receiving indole-3-carbinol," Nutr Cancer. 2001;41 (1-2):57-63.

Shilling et al., 2001, "3,3'-diindolylmethane, a major condensation product of indole-3-carbinol, is a potent estrogen in the rainbow trout," Toxicology and Applied Pharmacology 170:191-200.

Stresser et al., 1995, "Mechanisms of tumor modulation by indole-3-carbinol: disposition and excretion in male fisher 344 rats," Drug Metabolism and Disposition 23:965-975.

Stresser et al., 1995, "The anticarcinogen 3,3'-Diindolyl-methane is an inhibitor of cytochrome P-450," J. Biochem. Toxicol., 10(4):191-201.

Tse et al., 1987, "Disposition of alpha-[(dimethylamino)methy1]-2-(3-ethyl-5-methyl-4-isoxazoly1)-1H-indole-3-methanol (59-801), a hypoglycaemic agent in rats, dogs and monkeys," Xenobiotica, 17(6):741-9.

Walboomers et al., 1999, "Human papillomavirus is a necessary cause of invasive cervical cancer worldwide," J. Pathol. 189:12-19.

Yuan F et al., "Prevention of Papillomavirus initiated cancer by the phytochemical Indole-3-Carbinol", Proceedings of the $17^{th}$ International Papillomavirus Conference, Jan. 9-15, 1999, p. 73.

Zeligs MA, "Diet and Estrogen Status: The Cruciferous Connection", 1998, J Med Food, 1:67-82.

* cited by examiner

DIINDOLYLMETHANE FOR THE TREATMENT OF HPV INFECTION

CROSS-REFERENCE TO RELATED APPLICATIONS

This application is a divisional of U.S. patent application Ser. No. 10/117,288 filed Apr. 5, 2002, now U.S. Pat. No. 7,348,352 which claims the benefit of priority of U.S. Provisional Patent Application No. 60/337,563, filed Oct. 23, 2001, the disclosures both of which are hereby incorporated by reference in their entireties.

1. INTRODUCTION

The present invention relates to compositions and methods for the treatment of verrucae (common skin warts) and related, oral-genital infections with the human papilloma virus (HPV), using Diindolylmethane, a natural phytochemical found in cruciferous vegetables. The methods of the invention include the use of Diindolylmethane alone and in combination with immune potentiating steroids.

2. BACKGROUND OF THE INVENTION

2.1 Diindolylmethane

Diindolylmethane ("DIM") is a member of the family of dietary indoles discovered in cruciferous vegetables. Diindolylmethane and its unstable precursor, Indole-3-carbinol ("I3C"), have been identified in cruciferous vegetables, including broccoli, cauliflower, cabbage and Brussels sprouts (Bradfield, C. A. and Bjeldanes, L. F., "High performance liquid chromatographic analysis of anticarcinogenic indoles in *Brassica oleracea*", J. Agric. Food Chem., 35:46-49 (1987)). After the release of I3C from parent glucosinolates in cruciferous plants during crushing or chewing, Diindolylmethane is formed enzymatically. Also, Diindolylmethane is one of many indole products derived from I3C which are further generated during digestion as a result of acid-catalyzed reactions in the stomach and intestine.

2.2 Verrucae

Verrucae are common warts consisting of scaly rough nodules that can be found on any skin surface. They are benign proliferations most commonly involving the hands and soles of the feet. Their occurrence is related to epithelial infection with certain varieties of the Human Papilloma Virus ("HPV"). HPV activity is known to induce excessive skin and epithelial cell growth and result in visible lesions. With spread involving oral-genital epithelium, HPV activity results in wart-like lesions or flattened patches of abnormal epithelial surface showing characteristic, HPV-related, cellular changes microscopically (dysplasia). Once an individual has been infected, new warts and/or abnormal epithelia may develop in other sites of inoculation over a period of weeks to months.

2.3 SUMMARY OF PRIOR ART

Previous work with dietary indoles, including Diindolylmethane, has indicated their ability to impede the growth of estrogen sensitive breast cancer in animals (Chen, I., McDougal, A., et al., "Aryl hydrocarbon receptor-mediated antiestrogenic and antitumorigenic activity of Diindolylmethane", Carcinogenesis, 19(9):1631-39 (1998). These investigations resulted in U.S. Pat. No. 5,948,808 providing for a method of treating estrogen-dependent tumors. A second patent, U.S. Pat. No. 6,001,868, claimed other derivatives of I3C as a method to inhibit tumor cell growth, but specifically excluded Diindolylmethane.

I3C is known to be highly unstable and convert to a diverse family of metabolites. Many of these non-Diindolylmethane metabolites, and I3C itself, are known to have biologic activities. Many of the I3C condensation products such as ascorbigen (resulting from the combination of I3C and ascorbic acid), indolocarbazole (closed ring dimer), LTR (a linear trimer), and CTR (a cyclic trimer) are known to be absorbed and to be possibly useful in non-infectious processes. Prior clinical use of I3C and ascorbigen has been described to reduce the symptoms of fibromyalgia, a systemic chronic pain syndrome. This has resulted in U.S. Pat. No. 5,895,787. No relationship between fibromyalgia and cutaneous warts or HPV is known to exist.

Other published reports in the scientific literature have demonstrated possible usefulness of dietary supplementation with I3C in recurrent laryngeal papillomatosis and cervical dysplasia. The use of I3C in laryngeal papillomatosis was associated with cessation of papilloma growth in only 33% of patients and did not result in the disappearance of existing lesions in any patient. Furthermore, gastrointestinal and central nervous system side effects accompanied increasing the dose, making the 5-7 mg/kg of I3C dose a maximal tolerated dose and limiting further testing at higher doses. (Rosen, C. A., Woodson, G. E. et al., "Preliminary results of the use of indole-3-carbinol for recurrent respiratory papillomatosis", Otolaryngology Head Neck Surgery, 118:810-5 (1998)).

CIN describes "cervical intraepithelial neoplasia", an advanced form of cervical dysplasia and a pathologic diagnosis for cervical epithelial-changes which are known to be related to certain types of HPV. In the only study of I3C in CIN, 50% of treated patients (8 of 17) showed a normalized cervical biopsy after 3 months on either 200 mg/day or 400 mg/day of I3C. 50% of patients did not return to normal, and no increase in rate of response was observed in the higher dose group. (Bell, M. C., Crowley-Nowick, P., Bradlow, H. L., et al., "Placebo-controlled trial of indole-3-carbinol in the treatment of CIN", Gynecologic Oncology, 78:123-129 (2000). It is not known whether I3C itself or other biologically active, non-Diindolylmethane reaction products from I3C, account for the responses observed with oral I3C use in laryngeal papillomas or CIN. No reports exist as to the possible usefulness of Diindolylmethane in these or other HPV related processes.

Both Diindolylmethane and I3C have been used as dietary supplements since 1992 as cruciferous vegetable supplements, to benefit estrogen metabolism, and for potential cancer preventive action. Diindolylmethane is typically provided at a dose of 15 to 30 mg/day in an absorption-enhancing formulation due to its poor solubility. This results in a daily use of 60 to 120 mg of the absorption-enhancing formulation which is 25% Diindolylmethane by weight (Indolplex®, Enzymatic Therapy, Inc, Green Bay, Wis.). There are no reports as to the possible usefulness of either Diindolylmethane or I3C to beneficially influence cutaneous conditions. The clinical use of I3C as a treatment has been limited by the neurologic and gastrointestinal toxicity described at doses of more than 400 mg per day (Rosen, C. A., Woodson, G. E. et al., "Preliminary results of the use of indole-3-carbinol for recurrent respiratory papillomatosis, Otolaryngology Head Neck Surgery, 118:810-15 (1998)). Animal investigations using I3C at higher oral doses have revealed the undesirable activities of promoting unwanted estrogen metabolism (Ritter, C. L., Prigge, W. F., Reichert, M. A., Malejka-Giganti, D., "Oxidations of 17beta-estradiol and estrone and their interconversions catalyzed by liver, mammary gland and mammary tumor after acute and chronic treatment of rats with indole-3-carbinol or beta-naphthoflavone" Can. J. Physiol. Pharmacol., 79(6):519-32 (2001)) and a propensity to promote tumors in certain settings (Dashwood, R. H., "Indole-3-carbinol: anticarcinogen or tumor promoter in *brassica* vegetables?", Chem. Biol. Interact., 110(1-2):1-5 (1998)). Immune dysregulation, including reduced natural killer cell function has also been reported in association with I3C use (Exon, J. H., South, E. H., "Dietary indole-3-carbinol alters immune functions in rats." J. Toxicol. Environ. Health A., 59(4):271-9 (2000)).

Current treatments for verrucae involve physical destruction of the infected cells. The existence of multiple treatment modalities reflects the fact that none is uniformly effective or directly anti-viral. Treatment associated pain and risk of scarring are short-comings of skin cell destructive therapies. Topical treatments resulting in destruction of verrucae include freezing with liquid nitrogen, topical application of skin irritants such as podophyllin resin, and skin application of imiquimod, an irritant and immune stimulant. Other, less established treatments of cutaneous warts include high doses of the histamine antagonist cimetidine, representing the only oral medication of possible usefulness in this condition (Gooptu, C., et al., "Treatment of viral warts with cimetidine: an open-label study", Clin. Exp. Dermatol., 25(3): 183-5 (2000)). This use of cimetidine indicates further lack of understanding of the mechanisms needed to treat verrucae, since cimetidine is known to have an action on metabolism opposite to that of the dietary indoles (Michnovicz, J. J. and Galbraith, R. A., "Cimetidine inhibits catechol estrogen metabolism in women", Metabolism, 40(2):170-74 (1991)).

There is evidence that enhanced immuno-competence is associated with reduced severity of verrucae in humans. However immune-stimulating therapies with interferon have proven of limited efficacy as an isolated treatment. An alternative immune potentiating therapy has used the combination of cimetidine with the immune-stimulating drug levamisole in resistant cases of verrucae (Parsad, D., et al., "Comparison of combination of cimetidine and levamisole with cimetidine alone in the treatment of recalcitrant warts", Australas J. Dermatol., 40(2):93-5 (1999)).

Pregnenolone (PREG) and dehydroepiandrosterone (DHEA) are immune potentiating steroids produced in both the adrenal glands and the central nervous systems of mammals. These steroids are known to support healthy immune function. This action is related to support for cell mediated immunity contributed by DHEA (Khorram, O., et al., "Activation of immune function by dehydroepiandrosterone, (DHEA) in age-advanced men", J. of Gerontology: Medical Sciences, 52A(1): M1-M7 (1997)), and due to immune potentiating metabolites of both DHEA and PREG (Morfin, R., and Courchay, G., "Pregnenolone and dehydroepiandrosterone as precursors of native 7-hydroxylated metabolites which increase the immune response in mice", J. Steroid Biochem. Mol. Biol., 50:91-100 (1994)). Good thyroid function is also known to be required for active steroid production and metabolism contributing to immune function. Specifically, thyroid hormone functions to promote metabolism of DHEA, PREG, and estrogen to greater 2-hydroxy metabolites (Michnovicz, J. J., Galbraith, R. A., "Effects of exogenous thyroxine on C-2 and C-16 alpha hydroxylations of estradiol in humans", Steroids, 55(1):22-6 (January 1990)).

Concentrated extracts of the *Aloe Vera* species of plant are also known to be immunopotentiating (Pugh, N., Ross, S. A., ElSohly, M. A., Pasco, D. S., "Characterization of Aloeride, a new high-molecular-weight polysaccharide from *Aloe vera* with potent immunostimulatory activity", J. Agric. Food Chem., 49(2):1030-4 (2001)). This activity has been documented following both oral and topical use. Concentrates of these extracts with defined high molecular weight polysaccharides are known to have anti-viral activity (Gauntt, C. J., Wood, H. J., McDaniel, H. R., McAnalley, B. H., "Aloe polymannose enhances anti-coxsackievirus antibody titres in mice", Phytother. Res., 14(4):261-60 (2000)).

Immune dysfunction is a known contributor to HPV-related infections and to verrucae occurrence, growth, and spread. This is evidenced by increased verrucous disease in immunocompromized individuals, including but not limited to those with HIV infection, on cancer chemotherapy, and in immune-suppressed organ-transplant recipients. These individuals are known to have diminished levels of DHEA and pregnenolone, the primary immunopotentiating steroids. Additionally, cutaneous warts are worse in childhood when circulating levels of PREG and DHEA are at the lowest levels seen during the human life-span except for the severe declines which accompany aging and stress. Cutaneous warts are often noted to improve at the time of puberty in children when levels of PREG and DHEA rise.

Based on the lack of a well-tolerated, consistently effective, non-surgical approach to treatment of verrucae and related HPV conditions, new methods of treatment are needed. Ideally, such a treatment would be safe, cause the actual regression of existing lesions, work with natural immune processes, and be acceptable to the treatment of both children and adults.

3. SUMMARY OF THE INVENTION

The present invention relates to compositions and methods which include Diindolylmethane for the treatment of common warts and related oral-genital HPV infections. Common warts are most often present on the fingers and hands (palmar warts), or the soles of the feet (plantar warts). Oral-genital HPV infections involve the tongue, the oropharynx, the larynx, the peri-anal epithelium or uterine cervical epithelium (oral-genital epithelial dysplasias).

In a preferred embodiment, abnormal oral-genital epithelia and disfiguring and painful protrusions of thickened skin due to HPV (common warts) are caused to shrink and disappear during Diindolylmethane treatment using oral formulations of the phytochemical. In another embodiment, the combined use of topical or intralesional Diindolylmethane in combination with oral use of Diindolylmethane formulations results in the regression and disappearance of warts in an affected patient. In distinction to the standard ablative treatment of cutaneous warts using surgical excision, freezing, or caustic chemicals like imiquimod, the use of Diindolylmethane results in resolution without scarring or pain.

In certain embodiments, according to the present invention, uses of Diindolylmethane are provided which are clinically effective, different from prior dietary supplement uses, and associated with defined, minimum-necessary blood and tissue levels of absorbed Diindolylmethane. Also according to the present invention, pharmaceutical compositions are provided, which comprise Diindolylmethane in conjunction with immunopotentiators including PREG, DHEA, and *Aloe Vera* concentrates for enhanced verrucae treatment. These combined uses include a variety of Diindolylmethane, PREG, DHEA, and Aloe combinations, formulations, and pharmaceutically acceptable carriers.

4. DETAILED DESCRIPTION OF THE INVENTION

The present invention is based upon the observation that administration of Diindolylmethane results in the spontaneous remission, resolution and healing of common cutaneous warts (verrucae) and related oral-genital human papilloma virus (HPV) infections. Oral-genital infections benefited by Diindolylmethane treatment include HPV infections of certain epithelial surfaces adjoining the skin. These include the tongue, oropharynx, and larynx, as well as peri-anal infections and infections of the vagina and uterine cervix, including HPV-related vaginal and cervical dysplasia. In a particular embodiment, lesions caused by HPV infection are treated with Diindolylmethane.

Lesions caused by oral-genital human papilloma virus infections include oropharyngeal human papilloma virus-related papillomas and dysplasia, peri-anal human papilloma virus-related papillomas and dysplasia, vaginal human papilloma virus-related papilloma and dysplasia, and uterine cervical human papilloma virus-related papillomas and dysplasia. In preferred embodiments, the therapeutic dosages and preparations of the invention are well above those of the prior art and typical dietary supplementation levels. In preferred embodiments, effective uses of Diindolylmethane for HPV infections are identified which are associated with blood, urine and tissue Diindolylmethane levels at least than those seen with typical dietary supplement use of Diindolylmethane.

In a preferred embodiment, the use of Diindolylmethane in the present invention differentiates lower dose dietary supplement uses from higher dose HPV therapeutic uses by correlation of clinical responses at higher doses with associated blood levels in human subjects. These blood levels are clearly greater and distinguishable from the lower blood levels associated with low dose dietary supplement use. Results from direct plasma level assays of Diindolylmethane establish that blood levels of over 100 ng of Diindolylmethane per ml plasma are associated with therapeutic uses of 112 mg/day and above of oral Diindolylmethane. In preferred embodiments, a correlation between oral dosage level and resultant blood levels of Diindolylmethane is used to establish doses of Diindolylmethane useful for therapy of HPV-related disorders including verrucae and epithelial dysplasias. This correlation can be extended to required tissue levels of Diindolylmethane needed in association with topical or intralesional uses since tissue levels have been shown to resemble blood levels for related, poorly water soluble indole compounds. Tse, F. L., Orwig, B., Jaffe, J. M., Disposition of alpha-[(dimethylamino)methyl]-2-(3-ethyl-5-methyl-4-isoxazolyl)-1H-indole-3-methanol (59-801), a hypoglycaemic agent in rats, dogs and monkeys, Xenobiotica, 17(6):741-9 (June 1987).

Urine Diindolylmethane levels following oral dosing have also been used to establish appropriate dosage for HPV therapy.

The oral delivery of Diindolylmethane is facilitated and accomplished according to formulations and methods described in U.S. Pat. No. 6,086,915. The effectiveness of supplemental Diindolylmethane is further supported by oral or topical co-administration of Diindolylmethane with grapefruit concentrate, or other inhibitors of pre-systemic metabolism which additionally facilitates Diindolylmethane absorption and activity (Wang, E. J., et al., "Inhibition of P-glycoprotein transport function by grapefruit juice psoralen", Pharm. Res., 18(4):432-8 (2001)).

The treatment of cutaneous, oral, and genital manifestations of HPV infection with Diindolylmethane is further facilitated by topical and intra-lesional application of Diindolylmethane formulations in the form of tinctures, creams, vaginal or rectal suppositories, and injectable suspensions.

PREG and DHEA are used in combination with Diindolylmethane in treating verrucae. In preferred embodiments, such combination is used in subjects whose immune function may be compromised due to lower than optimal levels of immune-potentiating steroids as seen in childhood, infection, cancer, stress., and aging. In one embodiment, PREG alone is preferentially given with Diindolylmethane in childhood and both DHEA and PREG are given together with Diindolylmethane if warts accompany infections such as human immunodeficiency virus ("HIV"), cancer chemotherapy, aging, or other immunodefficient conditions. In another embodiment, PREG and Diindolylmethane without DHEA, is the preferred therapy for verrucae in children where elevations in androgenic and estrogenic metabolites from DHEA are undesirable. In another embodiment, PREG with Diindolylmethane is similarly used in young women and men with verrucae. Alternatively Diindolylmethane can be used in combination with non-estrogenic metabolites of DHEA available as supplements such as 7-Keto DHEA. Both older women and men suffering from verrucae benefit from the combined use of DHEA, PREG, and Diindolylmethane. In another embodiment, Diindolylmethane is used either orally or topically in combination with immunopotentiating concentrates of *Aloe Vera*. Diindolylmethane-*Aloe Vera* combinations can be used alone or with the addition of DHEA and/or PREG.

The synergistic interaction of Diindolylmethane, PREG, DHEA, and *Aloe Vera* Concentrates for improved therapy of verrucae is also an objective of the present invention.

4.1 Methods of Treating Verruca Vulgaris with Diindolylmethane

The invention provides compositions and methods for the treatment of common warts. In particular embodiments Diindolylmethane alone or in combination with PREG, DHEA, *Aloe Vera*, and with other dietary supplements, are administered orally in, for example, the form of encapsulated dietary supplements.

In preferred embodiments, Diindolylmethane is administered providing 112-750 mg per day of Diindolylmethane. In preferred embodiments, the dose of Diindolylmethane is 225 mg per-day.

In a preferred embodiment, Diindolylmethane is administered in an absorption enhancing formulation, as described in U.S. Pat. No. 6,086,915, providing 112-750 mg per day of Diindolylmethane suspended as microparticles in a starch carrier matrix. In another embodiment, the dose of absorbption-enhanced, processed Diindolylmethane is 450-3200 mg ("total formula weight") per day since, in a preferred embodiment, processed Diindolylmethane is 25% Diindolylmethane by weight.

Doses of the Diindolylmethane of the present invention can also be calculated based upon the body weight of the subject to be treated. Doses of Diindolylmethane at least 2 and up to 10 mg per kg of body weight per day are preferred. In another preferred embodiment, the phytochemicals are administered at a dose of between 2.5 and 5 mg per kg per day, between 5 and 10 mg per kg per day, between 3 and 7 mg per kg per day, preferably 2.5 mg per kg per day. In another preferred embodiment, the 2.5 mg per kg per day Diindolylmethane dose is administered in an absorption-enhanced formulation that is 25% Diindolylmethane by weight. This results in daily oral administration of 10 mg per kg per day of the formulation for a child weighing 30 kg, taken, for example, as two capsules each containing 150 mg of a 25% Diindolylmethane formulation. This can be increased in stages as clinically necessary up to maximal daily dose of 40 mg per kg per day of the formulation.

Alternatively, co-administration of Diindolylmethane with grapefruit concentrate can be used to increase absorption of the Diindolylmethane and promote even more efficient resolution of cutaneous warts. In children and young women with warts, Diindolylmethane is given with PREG and *Aloe Vera*. The PREG is used in a dose of 25 to 500 mg/day and the Aloe is used in a dried polysaccharide-rich extract in a dose of 500-1,500 mg/day administered by capsules, tablets, and in sustained release formulations. The combination is also administered transdermally. In older adults, PREG, DHEA, *Aloe Vera*, and Diindolylmethane are used together. The DHEA is used in a dose of from 5-200 mg/day in a fashion similar to PREG. PREG and DHEA are used alone and together in combination with Diindolylmethane according to the specific needs of individuals with verrucae and related HPV infections in need of treatment. The combinations are at times adjusted in view of results of serum, saliva, or urine testing for DHEA, PREG and Diindolylmethane.

Alternatively Diindolylmethane, *Aloe Vera* Concentrate, DHEA, and PREG may be administered alone or together in the form of transdermal creams applied directly to the skin. These creams utilize various absorption enhancing emollients and consist of Diindolylmethane, *Aloe Vera* Concentrate, PREG, and DHEA in concentration of 0.5-2% by weight. In preferred embodiments, the cream comprises Diindolylmethane in a concentration of 1-5%, from 1-3%, from 2-3%, or 1% by weight. PREG, DHEA, and *Aloe Vera* Concentrate are alternatively included alone or in combination with one another, or in combination with Diindolylmethane, or in combination with Diindolylmethane and one another, in concentrations of 0.25-2%. The cream is preferably designed as a moisturizing cosmetic that is formulated to allow application directly to warts.

In a preferred embodiment, the Diindolylmethane is administered both topically and orally, either simultaneously or within a short period of time of one another, preferably within 24 hours, 12 hours, 6 hours, 3 hours, 2 hours, 1 hour or 30 minutes of one another.

Alternatively, the phytochemical Diindolylmethane may be administered in the form of a vaginal cream or suppository containing microcrystalline Diindolylmethane suspended in vitamin-E TPGS (Eastman Company, Kingsport, Tenn.) in a daily dose of 200-1000 mg. This allows application of Diindolylmethane directly to vaginal mucosa for enhanced uptake and benefit of genital warts and related vaginal or cervical dysplasia. Suppositories can be formulated with Diindolylmethane alone or in combination with *Aloe Vera* Concentrate, PREG, or DHEA.

Alternatively, the phytochemical Diindolylmethane may be administered in the form of a rectal suppository containing microcrystalline Diindolylmethane suspended in vitamin-E TPGS (Eastman Company, Kingsport, Tenn.) in a dose of 200-1000 mg. This allows application of Diindolylmethane directly to rectal mucosa for enhanced uptake and benefit of peri-anal warts and related anal dysplasia. Suppositories can be formulated with Diindolylmethane alone or in combination with *Aloe Vera* Concentrate, PREG, or DHEA.

Alternatively, microcrystalline Diindolylmethane can be formulated in a sterile suspension for intralesional injection. Typically 100-200 mg of Diindolylmethane is suspended in 1 cc of sterile 0.9% NaCl solution and a portion injected in the dermis below a verrucous lesion. This allows slow dissolution of Diindolylmethane crystals providing a therapeutic tissue concentration.

The Diindolylmethane of the present invention may be administered in any appropriate amount in any suitable galenic formulation and following any regime of administration.

The actual administered amount of Diindolylmethane may be decided by a supervising physician and may depend on multiple factors, such as, the age, sex, condition, file history, etc., of the patient in question.

The subject, or patient, to be treated using the methods of the invention is an animal, e.g., a mammal, and is preferably human, and can be male or female, child, or adult.

4.2 Gas Chromatography—Mass Spectronomy Assays for Detecting Blood, Tissue and Urine Levels of Diindolylmethane The invention provides methods of using gas chromatography-mass spectrometry ("GC-MS") assays for determining Diindolylmethane in the blood and urine of a subject following administration of Diindolylmethane. Additionally, the techniques for the invention provide a method for determining the level of Diindolylmethane in the tissue of a subject. The following article is incorporated by reference in its entirety. Stresser, D. M., Bjeldanes, L. F., Bailey, G. S., et al., "The anticarcinogen 3,3'-Diindolylmethane is an inhibitor of cytochrome P-450", J. Biochem. Toxicol., 10(4):191-201 (1995). Particular attention is drawn to Mass Spectrometry Methods section of the article. Stresser, at p. 194.

The GC-MS method for determining the blood level of absorbed DIM in a subject following oral administration of Diindolylmethane demonstrates DIM in blood plasma or serum. The subject is preferably fasting and plasma is preferred over serum. In this method 120 mg or more of formulated DIM (30 mg or more of actual DIM) are taken orally by a subject fasting for at least 4 hours along with 8 ounces of water. Blood samples are obtained on a timed basis between 120 and 180 minutes after ingesting the DIM. Samples obtained during this timeframe are analyzed by a Gas Chromatography Mass Spectrometry (GC-MS) technique. Circulating amounts of DIM during this timeframe are maximal levels following a single dose. These results define therapeutic blood levels for HPV and approximate therapeutic tissue levels to actual DIM. The following steps describe the method for determining amounts of absorbed DIM in blood.

1. 120-180 minutes following ingestion of a Diindolylmethane formulation, a 5 cc venous blood sample is withdrawn from an arm vein into tubes containing standard Sodium Heparin anticoagulant.
2. The whole blood is centrifuged and plasma separated by pipet producing at least 2 cc of anti-coagulated plasma.
3. 500 ul of blood plasma is withdrawn from the plasma sample and added to 500 ul Tris buffer pH 9.1).
4. This mixture is extracted with 2.5 m. Ethyl Acetate twice.
5. The extracted mixture is centrifuged to combine the organic phase.
6. The sample is dried under nitrogen.
7. The sample is derivatized with 150 ul BSTFA ($N_2O$-bis-(timethyl-silyl)trifluoroacetamide):Pyridine (5:1) (Pierce Biochemical Co, Rockford, Ill.).
8. The derivatized sample is injected into a GC-MS apparatus in selected ion monitoring mode, using a 30M× 0.25 mm×0.25 um fil thickness HP1 column (Hewlett Packard, Menlo Park, Calif.). Initial temperature for GC-MS is 200° C. programmed at rate of 10 degrees/minute to 300° C. The following ions are monitored: m/z 390 (primary), 391,392 (confirmatory). Area for peak 390 is measured.

9. Peaks are compared to a standard curve for pure diindoylylmethane in known concentrations as a standard.
10. Results for each sample are reported as nanograms Diindolylmethane per milliliter of blood plasma (ng/ml).

The invention also provides a method for determining the urine level of DIM in a subject following oral administration of Diindolylmethane. In this method 300 mg or more of formulated DIM (75 mg or more of actual DIM) are taken with 8 ounces of water. Urine samples are obtained every 90 minutes for a period of 360 minutes. GC-MS operating conditions included were based on a published GC-MS analysis technique for DIM in urine (Sepkovic D W, Bradlow H L, Bell M, "Quantitative Determination of 3,3'-Diindolylmethane in the Urine of Individuals Receiving Indole-3-Carbinol" J. Nutrition (2002 in press). The following technique for analyzing DIM in urine samples was used:

1. A 1 cc aliquot of urine for assay of diindolylmethane is mixed with 1 cc of sodium acetate buffer (pH 4.8) and 20 ul Beta-Glucuronidase from *Helix Pomatia* (110,200 units/ml: Sigma, St. Louis, Mo.).
2. The solution is incubated at 40° C. for 24 hours.
3. An internal standard of 4,4'dichlorodiindolylmethane is then added.
4. The sample is then extracted in twice equal volume of chloroform and the sample vortexed and reduced to dryness under vacuum.
5. The dried residue is dissolved in 20 uL of anhydrous pyridine and derivatized with 80 ul of $N_2O$-bis-(timethyl-silyl)trifluoroacetamide (BFSTA) (Pierce Biochemical Co, Rockford, Ill.). The sample is heated to 100° C. for one hour.
6. The derivatized sample is then injected into a Gas Chromatography Mass Spectrometer (GC-MS) in single ion monitoring mode recording results at a derivatized mass of 390. The following ions are monitored: m/z 390 (primary), 391,392 (confirmatory). Area for peak 390 is measured.
7. Peaks are compared to a standard curve for pure diindoylylmethane in known concentrations as a standard.
8. Creatinine in each 90 minute timed urine sample was measured by a standard Kinetic Alkaline Picrate (KAP) colorimetric assay with results in mg of creatinine per cc of urine.
9. Results obtained for DIM from the 1 cc aliquot of each timed urine sample are reported as nanograms of DIM per mg of Creatinine. This permits comparisons of urine samples of different water content in different timed samples eliminating the effects of changing hydration status of the human subject.

Additionally, the above technique is adapted to analyze tissue excised from an experimental animal exposed to DIM. In this case, a 1 gram sample of tissue is homogenized in 3 cc of extraction solvent Ethyl Acetate containing 0.001% BHT) using a tissue homogenizer (Vortexer) at the highest speed. This mixture is then centrifuged at 10,000 g for 10 minutes. One half of the supernatant ethyl acetate, containing extracted DIM, is removed and reduced to dryness under vacuum. The residual is dissolved in 20 uL of anhydrous pyridine and derivatized with BFSTA (Pierce Biochemical Co, Rockford, Ill.). The derivatized sample in then injected into a Gas Chromatography Mass Spectrometer (GC-MS) in single ion monitoring mode recording results at a derivatized mass of 390. The following ions are monitored: m/z 390 (primary), 391, 392 (confirmatory). Area for peak 390 is measured. Peaks are compared to a standard curve for pure diindoylylmethane in known concentrations used as a standard. A doubling of the quantitative results for DIM in the derivatized sample provides the amount of DIM in nanograms per gram (ng/gm) of sampled tissue. In a preferred embodiment tissue levels of DIM from DIM administered orally or locally injected into tissue as a DIM suspension will be at least 200 ng/g of tissue.

In another preferred embodiment, the Diindolylmethane is administered to a subject in an amount that results in a Diindolylmethane blood level (measured in ng of Diindolylmethane per milliliter of plasma) of the subject at 120 minutes after administration of 60-1,000, 25-700, 75-300, 100-125, 100-110, about 105, at least 75, at least 85, at least 100, less than 1,000, less than 700, less than 125, at least about 75, at least about 75, at least about 85, at least about 100, less than about 1000, less than about 500, or about 125, as determined by the GC-MS-method.

In another preferred embodiment, the Diindolylmethane is administered to a subject in an amount that results in a Diindolylmethane blood level (measured in ng of Diindolylmethane per milliliter of plasma) of the subject at 150 minutes after administration of 60-1,000, 25-700, 75-300, 100-125, 100-110, about 105, at least 75, at least 85, at least 100, less than 1,000, less than 700, less than 125, at least about 75, at least about 75, at least about 85, at least about 100, less than about 1000, less than about 500, or about 125, as determined by the GC-MS method.

In another preferred embodiment, the Diindolylmethane is administered to a subject in an amount that results in a Diindolylmethane blood level (measured in ng of Diindolylmethane per milliliter of plasma) of the subject at 180 minutes after administration of 60-1,000, 25-700, 75-300, 100-125, 100-110, about 105, at least 75, at least 85, at least 100, less than 1,000, less than 700, less than 125, at least about 75, at least about 75, at least about 85, at least about 100, less than about 1000, less than about 500, or about 125, as determined by the GC-MS method.

In yet another preferred embodiment, the Diindolylmethane is administered to a subject in an amount that results in a peak Diindolylmethane blood level (measured in ng of Diindolylmethane per milliliter of plasma) of the subject of 60-1,000, 25-700, 75-300, 100-125, 100-110, about 105, at least 75, at least 85, at least 100, less than 1,000, less than 700, less than 125, at least about 75, at least about 75, at least about 85, at least about 100, less than about 1000, less than about 500, or about 125, as determined by the GC-MS method.

In a preferred embodiment, the Diindolylmethane is administered to a subject in an amount that results in a Diindolylmethane urine level (measured in ng of Diindolylmethane per milligram of Cre) of the subject at 180 minutes after administration of 3.5-7.0, 3.75-6.0, 4.0-5.0 ng/mg Cre as determined by the GC-MS method.

In a preferred embodiment, the Diindolylmethane is administered to a subject in an amount that results in a Diindolylmethane tissue level (measured in ng of Diindolylmethane per gram of tissue) of the subject at 120, 150 or 180 minutes after oral or intralesional administration and appropriate biopsy of 100-1,000, 200-700, 200-400, 60-1,000, 25-700, 75-300, 100-125, 100-110, about 105, at least 75, at least 85, at least 100, less than 1,000, less than 700, less than 125, at least about 75, at least about 75, at least about 85, at least about 100, less than about 1000, less than about 500, or about 125 ng/g, as determined by the GC-MS method. Preferably, the level of Diindolylmethane is achieved at the site of the lesion, particularly where the administration is topical or intralesional.

4.3 Pharmaceutical Compositions

The pharmaceutical compositions according to the present invention preferably comprise one or more pharmaceutically acceptable carriers and the active constituents. The carrier(s) must be "acceptable" in the sense of being compatible with the other ingredients of the composition and not deleterious to the recipient thereof.

It will be appreciated that the amounts of Diindolylmethane, and grapefruit concentrate required for said treatment will vary according to the route of administration, the severity of warty or HPV-related disease, age, and file history of the subject, the galenic formulation of the pharmaceutical composition, etc.

Preferably, the Diindolylmethane used in the invention has been processed to enhance bioavailability, as is described in U.S. Pat. No. 6,086,915; however any suitable preparation of pure diindolylmethane can be used in the methods and compositions of the invention.

In general, a suitable (therapeutically effective) amount of Diindolylmethane is preferably administered in an absorption enhancing formulation, as described in U.S. Pat. No. 6,086,915, at 112-750 mg per day as a suspension of microparticles in a starch carrier matrix. The actually administered amounts of Diindolylmethane may be decided by a supervising physician. The Diindolylmethane of the invention may be administered alone or in combination with other dietary supplements, and immunopotentiators, especially *Aloe Vera*, PREG and DHEA.

Therapeutic formulations include those suitable for parenteral (including intramuscular, intralesional, and intravenous), oral, rectal or intradermal administration, although oral administration is the preferred route. Thus, the pharmaceutical composition may be formulated as tablets, pills, syrups, capsules, suppositories, formulations for transdermal application, powders, especially lyophilized powders for reconstitution with a carrier for intravenous administration, etc.

The term "carrier" refers to a diluent, adjuvant, excipient, or vehicle with which the therapeutic is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin; and/or a flavoring agent, such as peppermint, methyl salicylate, or orange flavoring.

Therapeutic formulations suitable for oral administration, e.g., tablets and pills, may be obtained by compression or molding, optionally with one or more accessory ingredients. Compressed tablets may be prepared by mixing phytochemicals, and compressing this mixture in a suitable apparatus into tablets having a suitable size. Prior to the mixing, the phytochemical may be mixed with a binder, a lubricant, an inert diluent and/or a disintegrating agent.

In a preferred embodiment, Diindolylmethane is mixed with a binder, such as microcrystalline cellulose, and a surfactant, such as sodium lauryl sulphate until a homogeneous mixture is obtained. Subsequently, another binder, such as polyvidone, is transferred to the mixture under stirring with a small amount of added water. This mixture is passed through granulating sieves and dried by desiccation before compression into tablets in a standard tableting apparatus.

A tablet may be coated or uncoated. An uncoated tablet may be scored. A coated tablet may be coated with sugar, shellac, film or other enteric coating agents.

Therapeutic formulations suitable for parenteral administration include sterile solutions or suspensions of the active constituents. An aqueous or oily carrier may be used. Such pharmaceutical carriers can be sterile liquids, such as water and oils, including those of petroleum, animal, vegetable or synthetic origin, such as peanut oil, soybean oil, mineral oil, sesame oil and the like. Formulations for parenteral administration also include a lyophilized powder comprising phytochemical that is to be reconstituted by dissolving in a pharmaceutically acceptable carrier that dissolves said phytochemical.

When the pharmaceutical composition is a capsule, it may contain a liquid carrier, such as a fatty oil, e.g., cacao butter.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsions, tablets, pills, capsules, powders, sustained-release formulations and the like. The composition can be formulated as a suppository, with traditional binders and carriers such as triglycerides.

In yet another embodiment, the therapeutic compound can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)).

Other controlled release systems are discussed in the review by Langer (Science 249:1527-1533 (1990)).

In one embodiment of the pharmaceutical composition according to the invention, the Diindolylmethane, *Aloe Vera* Concentrate, PREG, and DHEA are comprised as separate entities. The four entities may be administered simultaneously or sequentially.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The invention is further explained by the following illustrative examples.

5. EXAMPLE

Manufacture of Processed Diindolylmethane for Enhanced Oral Bioavailability

Preparation of Processed Diindolylmethane was accomplished according to the steps outlined in U.S. Pat. No. 6,086, 915. Briefly, this included mixture of about 10-40% by final weight of either Diindolylmethane with about 10-40% by final weight of vitamin E polyethylene glycol 1000 succinate (Vitamin-E-TPGS, Eastman Chemical), 2-20% by final weight, phosphatidyl choline (Phospholipon 50G, Rhone Poulenc) and 15-30% by final weight hexanol. This mixture was made homogeneous by mixing. The homogeneous mixture of indoles and other oil soluble substituents listed above was added to a solution of modified starch in water (Capsul Starch from National Starch, Inc.). The starch component formed from 30-70% of the final dry weight of the product. The well dispersed final combined mixture was then subjected to spray drying. The resultant product was a fine powder containing Diindolylmethane contained within the starch particles.

6. EXAMPLE

Manufacture of Capsules Containing Diindolylmethane

Capsules containing 150-300 mg of processed Diindolylmethane, as produced according to the steps described in section 5, were made by mixing the processed Diindolylmethane with microcrystalline cellulose and placing the mixed powder into opaque gelatin capsules.

7. EXAMPLE

Manufacture of Diindolylmethane in a Cream for Transdermal Delivery

For the aqueous phase of the emulsion, a mixture of 70 grams of propylene glycol and 633 grams of water is heated to 95° C. The oil phase of the emulsion is prepared by heating a mixture of the following to 105° C.: 30 grams cetostearyl alcohol (Alfol 16/18, Vista), 30 grams hydrogenated soy monoglyceride (Myverol 18-06, Quest), 30 g. of a mixture of polyoxyethylene stearic acid ester and mono- and di-glycerides of fatty acids (Arlacel 165, ICI), 10 grams polyethylene (Epolene N-34, Eastman), and 50 g. of squalene. The active ingredient phase is prepared separately also by gently heating to about 63° C. a mixture of the following to uniformity: 30 g. d-Alpha-tocopherol polyethylene glycol 1000 succinate (Vitamin E TPGS, Eastman), 50 g. isopropyl myristate, and 15 g. of Diindolylmethane. The above oil phase is added to the aqueous phase using a rotor/stator type homogenizer at moderate speed. The mixture is cooled to 75° C. and 50 grams of lemon oil is added with low speed mixing followed by addition of the active ingredient phase. Lastly, 2 grams of a 3:1 mixture of methyl paraben to propyl paraben is added to the emulsion. This mixture is transferred to the reservoir of a high pressure homogenizer such as the Microfluidics Model 110Y. The emulsion is passed through the homogenizer approximately five times at 15,000 psi operating pressure that is sufficient to form a cream of the desired consistency which will not separate on standing.

8. EXAMPLE

Oral Use of Diindolylmethane for HPV Therapy

D. S. is a 20 year old woman with a 3 year history of abnormal Papinicolou Cervical Smears who was noted to have worsening of cervical HPV lesions. These lesions demonstrated moderate cervical dysplasia on cervical biopsy. She was begun on 75 mg/day of Diindolylmethane (300 mg/day total weight of a 25% absorbable formulation). After two months repeat Thin Prep cervical sample demonstrated persisting mild cervical dysplasia. The dose of Diindolylmethane was increased to 112 mg/day (450 mg/day total weight of the absorbable formulation). A repeat gynecologic examination after an additional month had returned to normal and repeat biopsy showed "squamous atypia" considered a normal finding. Follow up Papinoclou Cervical Smear obtained 4 months after the normal biopsy was read as within normal limits without further Diindolylmethane therapy.

9. EXAMPLE

Oral Use of Diindolylmethane for HPV Therapy

A. C., a 21 year old woman, was diagnosed with mild cervical dysplasia with HPV effect on histologic exam of cervical tissue. She began taking Diindolylmethane 60 mg/day, taken as 30 mg twice a day, using a total of 4 60 mg capsules/day of an absorbable Diindolylmethane formulation (Indolplex 60 mg, Enzymatic Therapy, Green Bay, Wis.). After two years on this daily regimen the dysplasia was noted to have worsened on repeat examination. Surgical excision of the lesions (LEEP procedure) has been recommended. The patient has been advanced to a daily dose of 150 mg/day of Diindolylmethane (600 mg/day of total formula weight of absorbable Diindolylmethane) and will be re-evaluated prior to surgery in 2 months.

This case demonstrates the therapeutic failure of chronic use of Diindolylmethane in the supplement dose range up to 60 mg/day (240 mg/day of 25% Diindolylmethane absorbable formulation).

10. EXAMPLE

Determinations of Diindolylmethane in Blood and Urine Following Oral Use for HPV Therapeutic Uses A gas chromatography-mass spectrometry (GC-MS) method for the quantitation of Diindolylmethane was developed to determine blood plasma and urine Diindolylmethane levels which follow the oral use of Diindolylmethane.

For blood level studies adult subjects were studied in a fasting state. On separate days, each subject provided a baseline blood sample and then orally consumed either a low dose of Diindolylmethane (30 mg) or a high dose (112 mg) with 8 ounces of water. Following this, blood samples were obtained every 30 minutes for 5 hours. Plasma was separated and frozen until analysis by GC-MS. Sample analysis using a technique for GC-MS measurement of Diindolylmethane, involving acetonitrile extraction, silyation, and GC-MS quantitation was performed as adapted from the literature (Stresser, D. M., Bjeldanes, L. F., Bailey, G. S., et al., "The anticarcinogen 3,3'-Diindolylmethane is an inhibitor of cytochrome P-450", J. Biochem. Toxicol., 10(4):191-201 (1995)) and described in section 4.2 above. Results for each sample were obtained in units of nanograms of Diindolylmethane per milliliter of plasma (ng/ml). A total of five experiments were done at the lower dose on three subjects by studying 2 subjects twice (n=5). All three subjects were studied once at the higher dose (n=3). Results from each time point were averaged and are presented in Table 1.

TABLE 1

Plasma Diindolylmethane ("DIM") levels after either a dietary supplement dose (30 mg) versus an HPV therapeutic dose (112 mg).

| | Time (minutes) | | | | |
|---|---|---|---|---|---|
| | 60 | 90 | 120 | 150 | 180 |
| Low Dose 30 mg (n = 5) | 30.34 ± 9.6 (s.e.m) | 34.72 ± 15.7 | 30.64 ± 7.6 | 27.72 ± 5.2 | 26.29 ± 5.7 |
| High Dose 112 mg (n = 3) | 49.66 ± 24.2 (s.e.m) | 75.79 ± 6.3 | 105.00 ± 2.6 | 109.39 ± 12.4 | 104.55 ± 17.7 |

Examination of the blood level results between 120 and 180 minutes reveals a clear difference according to dose level. An average plateau blood level for the 30 mg low dose of about 30 ng/ml was demonstrated, while a clearly higher average plateau blood level of 105 ng/ml was documented for the 112 mg high dose studies. This shows an augmentation of more than 3 times in Diindolylmethane blood levels from the low to high dose which bears a linear relationship to increasing the oral dose from 30 mg to 112 mg.

A related gas chromatography-mass spectrometry (GC-MS) method for the quantitation of Diindolylmethane in urine was developed. This technique is simpler, requiring less sample preparation but similar use of GC-MS analysis and provides results expressed as nanograms of Diindolylmethane per mg of Creatinine (ng DIM per mg Cre). Since production rates of Creatinine (Cre) are constant in an individual this technique allows comparison of urine samples from different times having differing water content. Sepkovic, D. W., Bradlow, H. L. Bell, M., Quantitative Determination of 3,3'-Diindolylmethane in the Urine of Individuals Receiving Indole-3-Carbinol, J. Nutrition (in press 2002).

A single individual was studied after taking 75 mg Diindolylmethane (300 mg of a 25% absorption-enhance formulation of Diindolylmethane) as a single dose after waiting 4 days since prior use of Diindolylmethane. Urine samples were collected every 90 minutes for a total of 360 minutes, frozen, and subsequently analyzed as described. Results are presented in Table 2.

TABLE 2

Urinary Diindolylmethane ("DIM") levels after a 75 mg oral dose.

| | Time (minutes) | | | |
|---|---|---|---|---|
| | 90 | 180 | 270 | 360 |
| Urinary DIM ng/mg Cre | 2.6 | 3.82 | 3.30 | 2.50 |

These results provide evidence of a plateau of urinary Diindolylmethane of 3.5 ng/mg Creatinine occurring around 180 minutes following oral dosing.

11. EXAMPLE

Oral Use of Diindolylmethane in Combination with Pregnenolone for Treatment of Cutaneous Warts The utility of dietary supplementation with the cruicferous phytochemical, Diindolylmethane in treating cutaneous warts (verrucae vulgaris) and its use in combination with pregnenolone is illustrated by the following case history.

K. W. is a 47-year-old woman who has had warts involving the fingers and palms of both hands. She also described several plantar warts on the soles of her feet. She had had the palmar warts frozen with liquid nitrogen by dermatologists several times but recurrence followed. She also treated the warts with over-the-counter medications that served to make her hands raw and sore but provided no significant resolution. In fact the proliferation continued after this therapy to a count of 40 warts on her right hand and 6 on her left hand. Since her hands were frequently cracked, bleeding, and painful she sought alternative therapy.

K. W. began taking Diindolylmethane at 75 mg/day in an absorption enhanced formulation 25% Diindolylmethane by weight (300 mg/day total formula weight). She progressively increased the dose to a maximum of 150 mg/day (total formula weight: 600 mg/day) over a period of 6 weeks without side effects. Pregnenolone at 50 mg/day in a capsule form was added for immune enhancement. No improvement had yet been noted. Shortly after this, initial improvement and shrinking of the warts was noted. Continuing with this combined use with the specified doses, progressive shrinkage of the palmar warts was noted.

After two months all warts were completely resolved and improvement and shrinkage in the plantar warts was also noted. Physical examination by her supervising physician revealed absence of warts on fingers and palms and no scarring. After a further month at the higher 150 mg/dose of Diindolylmethane dose and Pregnenolone 50 mg/day, she reduced her daily intake of Diindolylmethane to 75 mg/day (300 mg/day total formula weight) and has remained free of all palmar warts for 4 subsequent months.

12. EXAMPLE

Combined Oral and Transdermal Use of Diindolylmethane for the Treatment of Plantar Warts Plantar warts, or verrucae involving the soles of the feet, are a particularly difficult variety of verrucae to successfully treat. Surgical ablation in addition to topical caustic treatment of the underlying dermis revealed at surgery is typically required for long-term eradication. The contribution of dietary supplementation with the cruciferous phytochemical, Diindolylmethane in association with improved hormonal metabolism in treating plantar warts (verruca vulgaris) is illustrated by the following case history.

S. M. is a 62 year old female, who noted the onset of multiple plantar warts following a pedicure treatment which involved trimming of calluses on both feet with sharp instruments. This treatment was associated with skin breakage and some bleeding. One month following the pedicure treatment the patient noted multiple painful sites of abnormal skin growth on the soles of both feet characteristic of warts. These painful patches of raised skin continued to expand and failed to resolve following application of salicylic acid and imiquimod. Limited surgical excision was unsuccessful and resulted in recurrence at the site of surgery.

The patient initiated oral Diindolylmethane at 150 mg per day in an absorbable formulation (total formula weight: 600 mg/day. This was accompanied by twice daily application of Diindolylmethane in a 1% cream to the affected skin. Little response was noted for the first month of treatment. During this time the patient had been tested and was found to be hypothyroid. Thyroid replacement was initiated with Synthroid 25 ug per day. The oral dose of Diindolylmethane was increased to 187.5 mg per day of Diindolylmethane in an absorbable formulation (total formula weight: 750 mg/day). Shortly after the start of this use of Diindolylmethane at the increased dose combined with thyroid replacement, the lesions were noted to change in color to more white and gray, progressively shrink, and gradually resolve. Six to eight weeks after the dose increase, the lesions were completely gone and replaced by normal skin with no evidence of scarring. Normal skin lines were observed by the supervising podiatrist in the multiple locations previously occupied by verrucous tissue.

13. EXAMPLE

Use of Oral Diindolylmethane for the Treatment of Childhood Warts

The usefulness of oral forms of Diindolylmethane in treating verrucous disease of childhood is illustrated by the case of C. B. The subject is a 6-year-old boy with classic verrucae involving the plantar skin of one foot. The process began as a single wart, which was frozen with liquid nitrogen by a pediatrician. This resulted in blistering, inflammation, pain and healing into a flattened scar. Within 2 months, however, a new wart recurred at the sight of the original scar. Upon recurrence the primary lesion measured approximately 0.75 cm in diameter but was now circled by a number of smaller satellite lesions surrounding the recurrent primary wart.

Treatment was initiated with 75 mg/day of Diindolylmethane in an absorbable formulation (300 mg total formula weight). With the patient weighing 25 kg, this provided 3 mg/kg/day of Diindolylmethane and 12 mg/kg/day of the formulation. As documented by before and after treatment photographs, the warty lesions assumed a white to bluish color after two weeks of treatment and were fully resolved after 5 weeks of continuous Diindolylmethane use. There was no pain or scarring associated with the gradual resolution. No side effects associated with the oral treatment were noted.

14. EXAMPLE

Use of Diindolylmethane for Treatment of Oral Human Palilloma Virus Infection of the Tongue Administration of oral Diindolylmethane represents a novel and non-surgical method of treating HPV-related infections of the oropharynx. This was established in a case of visible, biopsy-proven, HPV infection of the tongue in a young woman.

C. A. V. is a 29-year-old woman who noted white spots on her tongue. These lesions were biopsied and found to be comprised of thickened squamous epithelium with papillomatous areas and inflammation. Suspected HPV involvement was confirmed by HPV DNA probe testing of the sample, which revealed presence of HPV DNA consistent with genotypes 6, 11, 42, 43, and 44. Photographs documented the untreated, spreading lesions and treatment with absorption-enhanced Diindolylmethane was begun 8 months after subject originally noted the white spots. The initial dose of 75 mg/day of Diindolylmethane (300 mg/day of the 25% Diindolylmethane absorbable formulation), resulted in clear improvement with reduction in lesion size after 2 weeks. However, a return of lesions were noted when therapy was suspended after one month.

Full resolution required resumption of treatment at an increased dose of 112 mg/day (450 mg/day of the 25% absorbable formulation). This was noted after a total of 2 months of oral therapy at the higher dose. No recurrence has been noted over a subsequent two-year period with continued use of absorption-enhanced Diindolylmethane at a dose of 37.5 to 75 mg/day (150-300 mg/day of the 25% absorbable formulation). A repeat swab of the treated and apparently normal tongue was negative for the presence of HPV DNA after two years of treatment. This case provided photodocumentation of a therapeutic response to doses of Diindolylmethane starting at 112 mg/day of Diindolylmethane.

15. EXAMPLE

Use of Diindolylmethane for Treatment of Genital Warts (Condyloma Accuminatum)

Oral use of Diindolylmethane has been demonstrated to provide a non-surgical, and non-irritating treatment for genital warts (condyloma accuminatum). This use is illustrated by the case of M. F., a 22-year-old woman who developed a progressive case of genital warts in association with mild cervical dysplasia. Genital warts were noted together with cervical inflammation during a routine gynecologic exam. A biopsy of the cervix and of a labial wart-like lesion returned the diagnoses of cervical dysplasia with HPV changes and condyloma accuminatum of the labia. The patient was initially treated with physician applied Tricarboxylic Acid (TCA) and patient applied Aldara Cream (Imiquimod). This resulted in pain and chronic irritation of great concern to the patient. Despite this therapy, the genital warts proliferated to entirely surround the introitus. Wishing to avoid surgery, the patient began formulated Diindolylmethane at 300 mg/day (75 mg/day of actual Diindolylmethane) and continued this for two months. Reexamination revealed no improvement, surgery was scheduled, but the dose of Diindolylmethane formulation was increased to 450 mg/day (112 mg/day of actual Diindolylmethane). 2 months later, pre-operative exam revealed the complete resolution of all genital warts and surgery was canceled. The uterine cervix also returned to a normal appearance and normal Papincolou Smear. The patient remained free of recurrent lesions 6 months later without further therapy. This case documents the minimal requirement for 112 mg/day of oral Diindolylmethane and the painless nature of resolution of genital HPV with Diindolylmethane therapy.

16. EXAMPLE

Use of Diindolylmethane for Treatment of Human Palilloma Virus-Related Cervical Dysplasia Closely monitored cases of HPV related cervical dysplasia were used to establish the efficacy of oral Diindolylmethane as a new, non-surgical therapy. Women with moderate to severe dyplasia on cervical biopsies volunteered for an open trial of oral Diindolylmethane supplementation. This degree of HPV induced dyplasia is known to be progressive if untreated and not associated with spontaneous resolution as sometimes occurs in some cases of mild dysplasia.

Four women, meeting the criteria of moderate to severe HPV-related cervical dysplasia were included in a pilot study. Based on the results of a cervical biopsy the four women began to take 450 mg/day of formulated Diindolylmethane. Based on a Diindolylmethane content of 25% by weight this represents 112 mg/day of actual Diindolylmethane. All four subjects demonstrated improvement as confirmed by repeat biopsy and improved physical exam of the uterine cervix. These benefits are summarized in the following table, which documents responses over treatment intervals of from 1 to 4 months.

TABLE 3

Summary of treatment with DIM and subsequent improvement of HPV-related cervical dysplasia in subjects A, B, C and D.

| | SUBJECT | | | |
|---|---|---|---|---|
| | A | B | C | D |
| Diagnosis | Cervical Dysplasia | Cervical Dysplasia | Cervical Dysplasia | Cervical Dysplasia |
| Age (yrs) | 20 | 62 | 26 | 27 |
| Dose (mg/day) | 450 | 450 | 450 | 450 |
| Treatment Interval (mo) | 4 | 1 | 2 | 1 |
| Biopsy Before DIM | Moderate Dysplasia CIN II | Severe Dysplasia CIN III | Moderate Dysplasia CIN II | Severe Dysplasia CIN III |
| Biopsy After DIM | Atypia | Atypia | Atypia | Mild Dysplasia CIN I |

The summarized treatment was associated with no significant side effects or adverse events. A darker more amber color of the urine was noted in some cases, consistent with absorption of Diindolylmethane, which is known to produce amber colored metabolites. Subjects specifically denied stomach upset, nausea or dizziness.

17. EXAMPLE

Use of Diindolylmethane for Treatment of Human Palilloma Virus-Related Vaginal Epithelial Dysplasia Local spread of HPV infection to involve the vaginal mucosa can accompany or follow HPV infection of the cervical epithelium. Vaginal HPV lesions require either repeated application of irritating chemicals or surgery to prevent spread and progression. The modalities have proven of limited efficacy, often requiring surgical intervention. Oral Diindolylmethane was used as an alternative in T. K., a 53-year-old woman with HPV-related vaginal dysplasia.

The patient was known to have mild cervical dysplasia as a young woman which resolved spontaneously. After bearing 2 children the patient was noted to have ovarian enlargement. Because of this, and a positive family for cervical cancer, she underwent total abdominal hysterectomy with oophorectomy at age 37 and began estrogen replacement therapy. Routine gynecologic exam at age 51 revealed inflamed vaginal mucosa at the site of the scar from removal of the uterus. This was biopsied and returned the diagnosis of moderate vaginal dysplasia. Supplementation with formulated Diindolylmethane was begun at 300 mg/day (75 mg/day of actual Diindolylmethane). A repeat biopsy was performed 3 months later and revealed persistent, moderate dysplasia indicating an inadequate therapeutic response to Diindolylmethane at 75 mg/day. The formulated Diindolylmethane dose was doubled to a total of 600 mg/day (150 mg/day of actual Diindolylmethane). A third biopsy performed one month later showed that the vaginal mucosa had returned to normal. Following this, the patient has lowered her daily dose of formulated Diindolylmethane to 150 mg/day (37.5 mg/day of actual Diindolylmethane) During this time at a sub-therapeutic, supplement level Diindolylmethane dose, the patient's physical exams have remained normal for 1.5 subsequent years.

18. EXAMPLE

Use of Oral Diindolylmethane to Treat Laryngeal Papillomatosis in a Child Previously Unresponsive to Indole-3-Carbinol (I3C)

The following describes oral Diindolylmethane therapy for the Recurrent Laryngeal Papillomatosis (RRP), a rare condition in which wart like lesions develop in and around the larynx and vocal cords in association with HPV.

A. L. is a 4 year old girl with RRP. She was diagnosed with RRP at 15 months of age. Before Diindolylmethane therapy she had undergone 21 laryngoscopic surgical procedures for recurrent laryngeal papillomas compromising her airway. During this time a 6 month oral use of I3C at 5-7 mg per kg failed to produce clinical improvement or a lengthening of the intervals between surgical procedures. Tracheostomy was performed in 1998 to provide a more secure airway. Diindolylmethane in an absorbable formulation according to U.S. Pat. No. 6,086,915 was begun in June 1998, at 2-3 mg/kg/day of Diindolylmethane. Surgical frequency increased immediately to two months. After 5 months of supplementation, existing papillomas had spontaneously resolved and no new papillomas were noted. 14 months past the start of Diindolylmethane, the patient underwent tracheal stenting, tracheostomy removal, and was found to be free of papillomas. While under subsequent anesthesia for adenoid surgery unrelated to RRP in March, 2000, the patient's larynx and trachea were examined and found still to be completely free of papillomas.

This case demonstrates the efficacy of oral use of Diindolylmethane for RRP in the 2-10 mg/kg/day dose range known to be therapeutic for HPV related disorders. Diindolylmethane also demonstrated the advantage of increased efficacy over I3C with I3C being used at its maximal, reported tolerated dose.

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, the disclosures of which are incorporated by reference in their entireties.

What is claimed is:

1. A method of treating human papilloma virus infection in a subject in need thereof, comprising administering to the subject an effective amount of Diindolylmethane (DIM), wherein the DIM is formulated as a tablet, pill, capsule, suppository, cream, parenteral suspension, or is suspended as microparticles in a starch carrier matrix.

2. The method of claim 1, wherein the DIM is formulated as a tablet.

3. The method of claim 1, wherein the DIM is formulated as a pill.

4. The method of claim 1, wherein the DIM is formulated as a capsule.

5. The method of claim 1, wherein the DIM is formulated as a suppository.

6. The method of claim 1, wherein the DIM is formulated as a cream.

7. The method of claim 1, wherein the DIM is formulated as a parenteral suspension.

8. The method of claim 1, wherein the DIM is suspended as microparticles in a starch carrier matrix.

9. The method of claim 1, further comprising administering to the subject a concentrate of *Aloe Vera*.

10. The method of claim 1, further comprising administering to the subject an immunopotentiating steroid, wherein the immunopotentiating steroid is dehydroepiandrosterone (DHEA), 7-Keto DHEA or pregnenolone (PREG).

11. The method of claim 1, wherein the effective amount of DIM is between 37.5 mg/day and 75 mg/day.

12. The method of claim 1, wherein the effective amount of DIM is between 75 mg/day and 112 mg/day.

13. The method of claim 1, wherein the effective amount of DIM is about 75 mg/day.

14. The method of claim 1, wherein the effective amount of DIM is about 112 mg/day or more than 112 mg/day.

15. The method of claim 1, wherein the effective amount of DIM is between 2 mg/kg/day and 10 mg/kg/day.

16. The method of claim 1, wherein the administering of the effective amount of DIM results in a peak blood plasma level of DIM in the subject of about or less than 125 ng of DIM per milliliter of plasma.

17. The method of claim 1, wherein the administering of the effective amount of DIM results in a blood plasma level of DIM in the subject of about or less than 125 ng of DIM per milliliter of plasma 120, 150 or 180 minutes after the administration of the DIM.

18. The method of claims 2, 3 or 4, wherein the DIM is administered orally.

19. The method of claim 5 or 6, wherein the DIM is administered transdermally.

20. The method of claim 5 or 6, wherein the DIM is administered vaginally.

21. The method of claim 5 or 6, wherein the DIM is administered rectally.

22. The method of claim 1 or 6, wherein the DIM is formulated for topical administration.

23. The method of claim 1, 9 or 10, wherein the subject has a human papilloma virus-related lesion selected from the group consisting of verrucae, recurrent laryngeal papillomatosis, oropharyngeal human papilloma virus-related papilloma, oropharyngeal human papilloma virus-related dysplasia, peri-anal human papilloma virus-related papilloma, peri-anal human papilloma virus-related dysplasia, vaginal human papilloma virus-related papilloma, vaginal human papilloma virus-related dysplasia, uterine cervical human papilloma virus-related papilloma, and uterine cervical human papilloma virus-related dysplasia.

24. The method of claim 23, wherein the effective amount of DIM is between 37.5 mg/day and 75 mg/day.

25. The method of claim 23, wherein the effective amount of DIM is between 75 mg/day and 112 mg/day.

26. The method of claim 23, wherein the effective amount of DIM is about 75 mg/day.

27. The method of claim 23, wherein the effective amount of DIM is about 112 mg/day or more than 112 mg/day.

28. The method of claim 23, wherein the effective amount of DIM is between 2 mg/kg/day and 10 mg/kg/day.

29. The method of claim 23, wherein the administering of the effective amount of DIM results in a peak blood plasma level of DIM in the subject of about or less than 125 ng of DIM per milliliter of plasma.

30. The method of claim 23, wherein the administering of the effective amount of DIM results in a blood plasma level of DIM in the subject of about or less than 125 ng of DIM per milliliter of plasma 120, 150 or 180 minutes after the administration of the DIM.

31. A method of treating human papilloma virus infection in a subject in need thereof, comprising administering to the subject an effective amount of Diindolylmethane (DIM), wherein the effective amount of DIM is between 2 mg/kg/day and 10 mg/kg/day.

* * * * *